United States Patent
Haslwanter et al.

[11] Patent Number: 5,948,392
[45] Date of Patent: Sep. 7, 1999

[54] STABLE SULFIDE COMPOSITIONS, USES, AND PROCESS FOR PREPARATION THEREOF

[75] Inventors: Joseph A. Haslwanter, Germantown; Gerald R. Dever, Cordova, both of Tenn.; Thomas J. Laughlin, Grapevine, Tex.

[73] Assignee: Schering-Plough HealthCare Products, Inc., Memphis, Tenn.

[21] Appl. No.: 08/452,451

[22] Filed: May 26, 1995

Related U.S. Application Data

[63] Continuation of application No. PCT/US94/00435, Jan. 25, 1994, which is a continuation-in-part of application No. 08/011,025, Jan. 29, 1993, abandoned.

[51] Int. Cl.[6] .............. A61K 7/04; A61K 9/10; A61K 33/04; A61K 47/38
[52] U.S. Cl. .............. 424/61; 424/488; 424/706; 424/707
[58] Field of Search .............. 424/61, 484, 488, 424/706, 707, 400

[56] References Cited

U.S. PATENT DOCUMENTS

| | | | |
|---|---|---|---|
| 1,379,853 | 5/1921 | Donner | 451/48 |
| 2,031,489 | 2/1936 | Koenigsberger | 167/89 |
| 2,487,558 | 11/1949 | Kamlet | 167/89 |
| 3,864,294 | 2/1975 | Busch, Jr. | 260/285 A |
| 4,073,887 | 2/1978 | McLean, Sr. | 424/147 |
| 4,110,230 | 8/1978 | Hessert et al. | 252/855 R |
| 4,755,195 | 7/1988 | Compton et al. | |
| 4,854,333 | 8/1989 | Inman et al. | 132/209 |
| 5,089,509 | 2/1992 | Chandraratna | 514/337 |

FOREIGN PATENT DOCUMENTS

| | | |
|---|---|---|
| A 670039 | 11/1929 | France . |
| A 1170558 | 1/1959 | France . |
| A 1483314 | 4/1966 | France . |

OTHER PUBLICATIONS

The Merck Index, 10th Edition, Merck & Co., Rahway, N.J., Entry 8527. Sodium Sulfide, p. 8526.

Cosmetics, Science & Technology, Edward Sagarin (ed.) Interscience Publishers, New York, 1957, Chapter 20–Depilatories, pp. 457–478.

H.M. Fishman, "Depilatories," HAPPI, Feb. 1989, pp. 34–35.

Aqualon Technical Bulletin Natrosol® Hydrdoxyethylcellulose, Aqualon Company, 1313 North Market Stree, Wilmington, DE, (rev. Jul. 1987) 22 pages.

M. DeLa Guardia, "Facial depilatories on black skin", Cosmetics and Toiletories, vol. 91, Jul. 1976, pp. 37–38.

*Primary Examiner*—Edward J. Webman
*Attorney, Agent, or Firm*—Joseph T. Majka

[57] ABSTRACT

Stable sulfide-containing compositions have been developed. The stable sulfide-containing composition comprises a) a sulfide, a polysulfide or mixtures thereof, of an alkali or an alkaline earth metal, and b) a carrier, such that after maintaining the sulfide-containing composition at a temperature of about 37° to about 50° Celsius for about 2 weeks to one month, the sulfide content remaining in the sulfide-containing composition is about 90% or greater of the initial sulfide content. The sulfide-containing compositions can be used for relieving the pain of ingrown toenail by softening the nail, or as a depilatory for removing human hair or hair from animal hides.

16 Claims, 2 Drawing Sheets

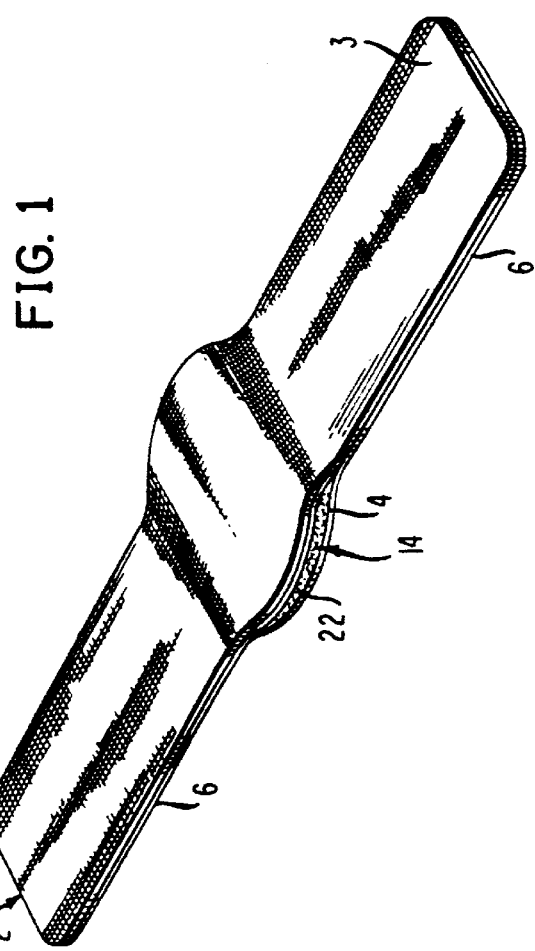
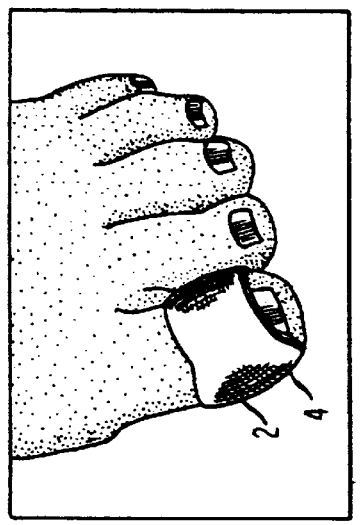
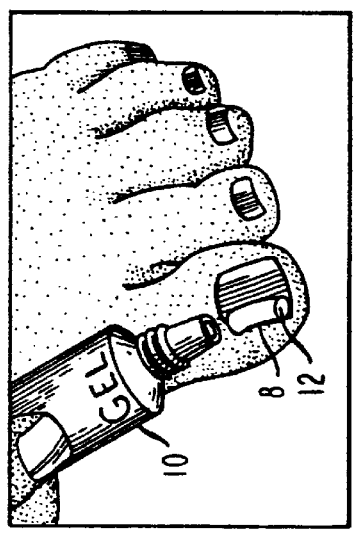
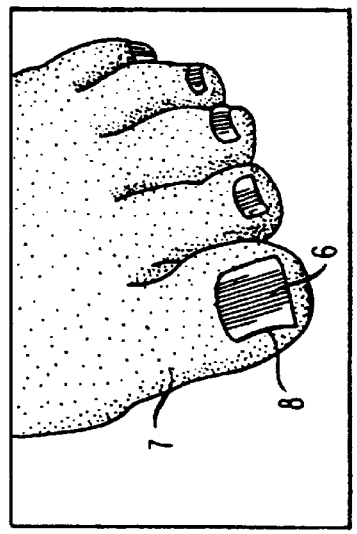

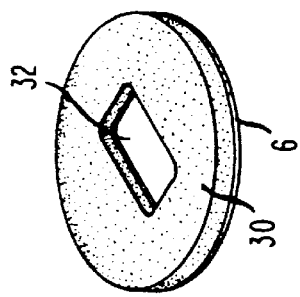
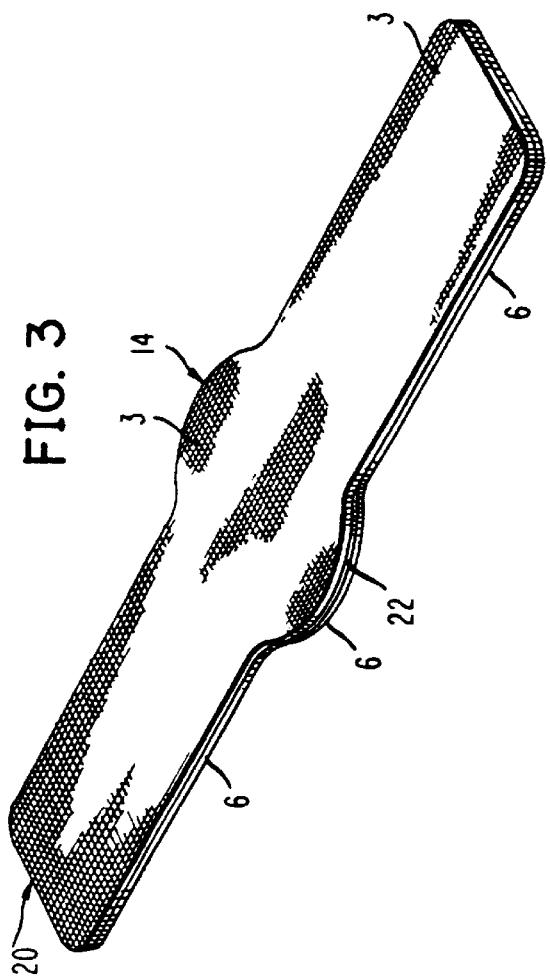
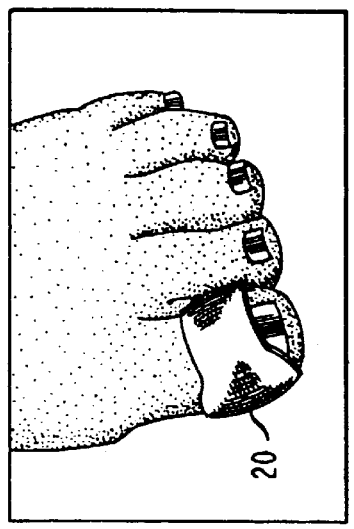
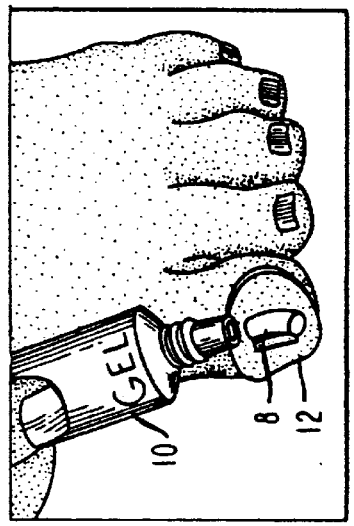
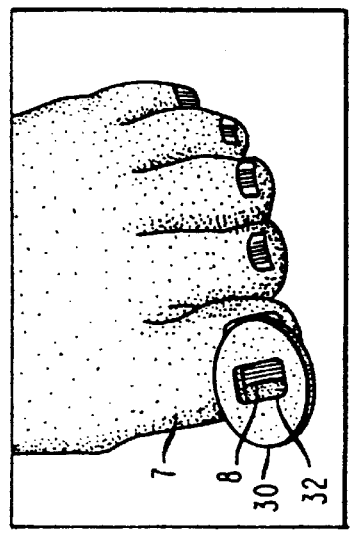

STABLE SULFIDE COMPOSITIONS, USES, AND PROCESS FOR PREPARATION THEREOF

CROSS REFERENCE TO RELATED APPLICATIONS

This application is a continuation of International Application No. PCT/US94/00435, filed Jan. 25, 1994 and designating the United States, which PCT application is in turn a continuation-in-part of U.S. application Ser. No. 08/011,025, filed Jan. 29, 1993, the benefit of which applications are claimed pursuant to the provisions of 35 U.S.C. 120, 363 and 365(C).

BACKGROUND

Sulfides, such as sodium sulfide nonahydrate (hereinafter referred to as sodium sulfide), are effective keratolytic agents useful for softening nails and as depilatory agents for removing unwanted hair. Cosmetics, Science and Technology, Edward Sagarin (Ed.) lnterscience Publishers, a division of John Wiley & Sons, New York, (1957) in the Chapter 20 Depilatories by Richard H. Barry, on pages 457–478 provides an historical review on the use of sulfide-containing depilatories. A long-standing problem exists in this art, however. Sulfides tend to be extremely unstable during storage and numerous attempts have been made to stabilize this class of compounds. For example, there are numerous references which teach allegedlly stabilized sufide compositions, such as U.S. Pat. No. 1,379,855 (1921) to J. Donner, U.S. Pat. No. 2,031,489 (1936) to F. Koenigsberger and U.S. Pat. No. 2,487,558 (1949) to J. Kamlet. However, none of these references provides a process for effectively carrying out the preparation of a sulfide-containing composition in the substantial absence of decomposing or oxidizing agents such as oxygen, carbon dioxide and various metallic impurities which can rapidly decompose the sulfide in the composition during preparation, storage or use. Thus, the decomposition renders the sulfide-containing compositions ineffective for their intended uses. Accordingly, a different approach was needed to provide truly stable, sulfide-containing compositions.

SUMMARY OF THE INVENTION

The present invention is directed toward a stable sulfide-containing composition comprising:
a) a sulfide, a polysulfide or mixtures thereof, of an alkali or an alkaline earth metal; and
b) a carrier, such that after maintaining the sulfide-containing composition at a temperature of about 37° to about 50° Celsius for about 2 weeks to one month, the sulfide content remaining in the sulfide-containing composition is about 90% or greater of the initial sulfide content.

Preferably the sulfide is a sulfide of an alkali earth metal, most preferably sodium sulfide. Also preferred is that the carrier for the sulfide is a gel. More preferably the gel contains a non-ionic cellulosic material, such as hydroxyethyl cellulose.

The present invention is also directed toward a process for preparing the stable sulfide-containing composition of claim 1, comprising contacting, in the substantial absence of agents which can decompose the sulfide in the composition and in the presence of an inert atmosphere, a sulfide, a polysulfide or mixtures thereof, of an alkali or an alkaline earth metal, with a suitable carrier. Preferably, the removal of agents which can decompose the sulfide in the composition is performed by removing gases in water by using a vacuum and by introducing an inert atmosphere, prior to addition of the sulfide. The mixing of the sulfide with any other ingredients in the composition is also conducted under an inert atmosphere.

The present invention is also directed toward a medicament for softening nails or for treating ingrown toenail. The medicament comprises or is made of the stable sulfide composition as described above.

The present invention is also directed toward the use of a stable sulfide-containing composition as described above, for the manufacture of a medicament for softening nails or for treating ingrown toenail.

The present invention is also directed towards a method for softening nails or for treating ingrown toenail. The method comprises contacting the nail with our stable sulfide composition as described above, for a time effective to soften the nail. Optionally, the nail or ingrown toenail may be trimmed.

The present invention is also directed towards novel delivery systems for applying the sulfide-containing gels for treatment of ingrown toenail.

The sulfide-containing compositions of the present invention can be used for medicinal purposes, such as an agent to treat onychocryptosis, a nail condition in which the lateral edge of the nail plate pierces the tissue in or directly under the lateral nail fold (ingrown toenail). Applications of the sulfide-containing composition can soften the nail, permitting the nail to be lifted out of the nail groove and trimmed, thus relieve the pain from an ingrown toenail or an ingrown fingernail. The present composition can also be employed to soften nails in order to promote penetration of other drugs, such as salicylic acid for treating onychomycosis (fungal nail) or retinoids such as tretinoin (Vitamin A acid) for promoting nail growth. The present composition can also be used as a depilatory agent to cosmetically or medically remove body hair, such as from the face, neck, arms, legs, back, underarms or groin. For example, the present composition may be useful in removing body hair as preparation prior to surgery. Another use of the present composition includes its use as an agent to relax and/or straighten curly, frizzy or wavy hair. Alternatively, the present composition can also be used to curl naturally staight hair by mechanically curling the hair, chemically softening the hair, then neutralizing the treated hair. The present invention can also be employed as a keratolytic agent for treating various dermatologic conditions, eg. corns, calluses, dry flaking skin, scale-like skin such as from psoriasis and the like.

The present invention has numerous industrial applications. For example, in the animal skin tanning industry, the present compositions can serve as a depilatory agent for removing hair from animal hides, particularly for the manufacture of leather goods. Other industrial applications include the desulfurizing of viscose rayon, the reprocessing of rubber, the manufacture of sulfur dyes, in ore floatation, metal refining, engraving or in cotton printing.

The present invention has the advantage of providing a sulfide composition in which the stability of the sulfide active ingredient is greatly improved under accelerated aging and normal shelf-life conditions. Such improvement in stability renders this class of compounds available for all of the above-cited applications. A second advantage of the present invention is that it can provide sufide-containing compositions as clear gels or liquids, enabling the user to readily see when the softened hair and sulfide-containing composition is ready for removal by wiping followed by washing of any residual gel off the skin. Another advantage of the present invention is that it provides a stable composition and a method for softening ingrown toenails, which allows the ingrown toenail to be lifted out of the nail groove and trimmed, eliminating the painful condition.

DETAILED DESCRIPTION OF THE INVENTION

The phrase "initial sulfide content" refers to either:

1) the sulfide content of the sulfide-containing composition prior to exposure or 2) the sulfide content stated on a product label for a sulfide-containing composition.

Sulfides of alkali earth metals include lithium sulfide, sodium sulfide and potassium sulfide. Sulfides of alkaline earth metals include cesium sulfide, magnesium sulfide, calcium sulfide, strontium sulfide, barium sulfide. The sulfide can be employed in an amount effective to impart the requisite nail softening or depilatory properties. For uses such as softening a toenail or fingernail, such amounts can range from about 0.01 to about 10%(wt/wt of composition), preferably from about 0.5 to about 5%, more preferably from about 1 to about 3 %. Where sulfide is to be used for penetration enhancement of active ingredients, the amount of sulfide can range between about 0.1 to about 1%, preferably from about 0.5 to about 1.0%. Where the sulfide is to be used as a depilatory, the amounts of sulfide can range from about 0.5 to about 5%. Percentages given are based upon sodium sulfide nonahydrate.

The term "gel" refers to any high-viscosity aqueous formulation of water soluble polymers.

The term "carrier" refers to any aqueous or water-containing formulation within which the sulfide is dissolved or dispersed. Suitable carriers include aqueous or water-containing formulations of water-soluble, modified (eg.hydroxylated) cellulosic materials such as hydroxymethylcellulose, hydroxyethylcellulose, hydroxypropylcellulose; polyvinyl alcohol; polyethylene oxides; guar gums; polyacrylic and polymethacrylic acids; polyvinylpyrrolidinone and the like. Other carriers which can be employed include nonionic emulsifying waxes NF which contains cetostearyl alcohol and polyoxyethylene derivatives of a fatty acid ester of sorbitan; silicone oils; glycols such as ethylene glycol and propylene glycol; carbonates of the alkaline earth metals such as calcium or magnesium carbonate; oxides of alkaline earth metals such as calcium oxide, magnesium oxide, zinc oxide and titanium oxide; or stearates such as calcium magnesium stearate.

An especially preferred gel can be formulated from a non-ionic water soluble polymer known as Natrosol® R-grade, trademark of Aqualon Company, Wilmington, Del. Chemically, Natrosol is cellulose that has been etherified with hydroxyethyl groups to give the desired properties. The R grade is designated as an easy-dispersing form formed by treating hydroxyethylcellulose with a coating of glyoxal. The R materials have been treated to delay hydration of the particle and thus prevent lumping as the dry powder is added to water, according to Aqualon Product Data, Number 401-11. Natrosol 250R is a white to light tan, tasteless, free-flowing granular powder. The powder is insoluble in organic solvents and is easily dissolved in cold or hot water to give nonionic solutions of varying viscosities. A 1% aqueous solution of this polymer is able to maintain a viscosity of between about 1500 to about 2500 centipoise (CPS) at 25° C. over a solution pH ranging from 2 to 12. Similarly, other Natrosol grades can be used, such as Natrosol 250 HHR, 250 MR or 250 KR.

Where a polymer is employed, the amount of polymer in the carrier can range from about zero percent (eg. a sulfide-in-water solution or formulation) to about 15 percent, preferably from about 0.25 to about 10%, more preferably from about 3 to about 7%, most preferably from about 4 to about 5%.

The viscosity of the sulfide-composition can be adjusted to any desireable consistency and viscosity using carrier ingredients based upon product requirements.

The water used in the present composition should be substantially free of all dissolved metallic ions, salts and other dissolved impurities. Preferably the water is deionized and/or distilled. The amount of water in the composition can range from about 5 to about 99%, preferably from about 70 to about 97%, more preferably from about 90 to about 97%, most preferably about 90%.

Optionally, a perfuming agent can be added to composition of the present invention. Suitable perfuming agents include those based upon terpenes and other hydrocarbons, some types of unreactive alcohols, ethers, ketones and on such specific perfuming agents such as the oils of vetivert, patchouli, thyme, lavender, lemon, citronella cedarleaf, caraway and synthetics such as ionone, safrole, vanillin, menthol, diphenylmethane. Preferably the perfuming agent is phenylethyl alcohol or benzyl alcohol.

The ingredients in the sulfide-containing composition can be combined using conventional mixing equipment suitably designed for mixing under vacuum and in an inert atmosphere, such as a Ross Anchor VersaMix multiagitator mixer, trademark of the Charles Ross & Son Company, Hauppauge, N.Y.

A substantial absence of decomposing agents, eg. oxygen or carbon dioxide, in the mixture can be accomplished using conventional procedures such as initially degassing the water with vacuum while introducing a partial pressure of an inert atmosphere prior to addition of any of the ingredients, (except for an optional antioxidant), such as the sulfide reagent. After degassing of the water is complete, a vaccuum can be reapplied to the mixing vessel, an inert gas bleed can be introduced to assure that the decomposing agents are not introduced into the mixing vessel. An inert atmosphere can be provided with any suitable gas, such as nitrogen, helium, neon, argon or mixtures thereof. Alternatively, the water can be sparged with an inert gas, boiled or any combinations of the above to provide for the substantial absence of decomposition agents in the water or mixture.

Optionally, the present composition can also contain chelators or chelating agents such as disodium ethylene diamine tetraacetic acid (EDTA) for scavanging iron and other metal impurites from the water and/or mixing vessel.

The composition can be maintained in a pH of between about 8.5 to about 13.5, more preferably a pH of between about 11 to about 13.5.

Analytical Method for Determining Sufide Content a. Preparation of Sulfide Antioxidant Buffer (SAOB). Eighty grams of sodium hydroxide is dissolved in 500 ml of water, and the solution is allowed to cool to room temperature. To this solution 67.2 g of disodium EDTA is added. Water is then added to bring the solution to a volume of 1000 ml. Just prior to use, mix 17.9 g of ascorbic acid to 500 ml of the NaOH/EDTA solution to give SAOB.

b. Determining Sulfide Content. Two grams of a sample gel are dissolved in 100 ml of SAOB. A sample of the resultant solution is titrated with 0.01 M lead perchlorate and the endpoint is determined potentiometrically with a suitable autotitrator equipped with a silver/sulfide electrode and a double junction reference electrode containing saturated silver chloride (inner fill) and 10 percent (%) potassium nitrate (outer fill). The sodium sulfide nonahydrate content ($Na_2S \cdot 9H_2O$) can be calculated using the following formula:

$$\frac{\text{(Molarity of Titrant)(mL of Titration)(80.008)}}{\text{(g of sample)}} = \% \text{ w/w of } Na_2S \cdot 9H_2O$$

The precision of the method is ±2%.

The following examples serve to illustrate the compositions and the manner by which the invention can be practised.

EXAMPLE 1.

Preparation Of A Stable Sulfide-Containing Composition

In the following example, the ingredients are measured on a percent weight ingredient /weight of composition (% wt/wt). To a Ross Anchor type mixer bowl is added 90.87 percent of deionized water and 0.02 percent disodium EDTA. The mixer bowl containing the solution is covered and the solution is agitated under vacuum to remove entrapped air, including oxygen and carbon dioxide, in the water. To the EDTA-containing solution, 3 percent of potassium acetate is added. The mixer bowl is again covered, a vaccuum is applied, and nitrogen gas is dispersed into solution. To this solution, 1.11 percent sodium sulfide nonahydrate is added, the mixer bowl is covered and nitrogen gas is dispersed into the solution and the solution agitated. To this solution, 5.00 percent Natrosol 250 HR is added, a vacuum is applied, and the solution again agitated. Nitrogen gas is introduced into the mixing bowl to purge any gases from the mixing bowl headspace, a vacuum is applied and the resultant sulfide-containing composition is agitated under nitrogen atmosphere to uniformly mix all ingredients, giving a bubble-free sulfide-containing gel.

EXAMPLE 2

Testing The Stability Of A Sulfide-Containing Composition

Plastic tubes are filled with a sample of a sulfide-containing gel having an initial sulfide content of 0.89% (wt/wt). The openings of the tubes are heat sealed. The tubes are exposed to temperatures of room temperature (ambient), 37° C., and 50° C. for a period of one month and the sulfide content is analyzed. Results are presented in Table. 1.

TABLE 1

Stability of Sulfide-Containing Composition After One Month Storage

| Temperature | % Sodium Sulfide Nonahydrate After one month (initial = 0.89%) | Relative % of Initial Sodium Sulfide Nonahydrate Remaining |
| --- | --- | --- |
| Room | 0.885 | 99.4 |
| 37° C. | 0.850 | 95.5 |
| 50° C. | 0.830 | 93.3 |

BRIEF DESCRIPTION OF THE DRAWINGS

FIGS. 1, 2a–c and FIGS. 3, 4, 5a–c represent two delivery systems for applying the sulfide-containing gels for treatment of ingrown toenail.

FIG. 1 shows a bandage 2 for retaining the sulfide-containing gels of the present invention on the ingrown toenail area.

FIGS. 2a, 2b and 2c show a representative method for using bandage 2.

FIGS. 3 and 4 show a bandage wrap 20 and retainer ring 30, respectively for applying the sulfide-containing gels of the present invention to an ingrown toenail.

FIGS. 5a, 5b and 5c show a representative method for using bandage wrap 20 and retainer ring 30.

In FIG. 1, bandage 2 is comprised of a strip 3 coated on one side with pressure sensitive adhesive 6, such as an acrylic adhesive. Strip 3 should be made of a breathable polymeric material, such as a woven tricot cloth. Strip 3 has a central portion 14, the underside to which is attached an occlusive patch 22. Occlusive patch can be made of any suitable moisture-blocking material, such as polyethylene foam or vinyl film. Occlusive patch 22 also has an adhesive on its underside, to which absorbent material 4 is attached. Absorbent material 4 can be made of a suitable fiber such as non-woven rayon acetates.

In FIG. 2a, foot 7 is depicted as having an ingrown toenail plate 6 which pierces the nail groove 8. In FIG. 2b, the sulfide-containing gel 12 from tube 10 has been squeezed into nail groove 8. In FIG. 2c, the gel is covered with bandage 2. Bandage 2 retains gel 12 in the area of nail groove 8 on the toe.

In FIG. 3, bandage wrap 20 is comprised of strip 3 coated on one side with a pressure sensitive adhesive 6. Strip 3 has a central portion 14 to which is attached an occlusive patch 22. Occlusive patch 22 also has an adhesive on its exposed underside.

In FIG. 4, retainer ring 30 has a rectangular shaped slot or aperture 32. Retainer ring 30 should be an essentially inert material, such as a low density polyethylene foam. The retainer ring can vary from 0.5 millimeters to 2 millimeters in thickness. Retainer ring 30 is used to protect the skin and retain the sulfide-containing gel in place on the afflicted ingrown toenail area. Underside 6 of retainer ring 30 has a pressure sensitive adhesive for attaching to the toe.

In FIG. 5a, aperture 32 of retainer ring 30 is aligned with the afflicted nail groove 8 of the ingrown toenail. In FIG. 5b, the sulfide-containing gel 12 from tube 10 has been squeezed so as to fill the slot or aperture 32 of retainer 30 over nail groove 8. In FIG. 5c, gel 12 and retainer ring 30 are covered with occlusive bandage wrap 20 wrapped around the toe.

EXAMPLE 3

In Vitro Nail Softening With Sodium Sulfide Formulation

To determine the usefulness of our new formulation for softening nails, sodium sulfide formulations having an initial sulfide concentrations of 1.0% and 2.0% prepared in accordance with the present invention, are applied to cut nails. Results are presented in Table 2.

TABLE 2

Time for cut nails treated with NaS formulation to soften.

| Initial Content of Sodium Sulfide Nonahydrate Hydrogels | Time to Soften | |
| --- | --- | --- |
| | 50% Softening | 75% Softening |
| 1.0% | 1.3 hours | 3 hours |
| 2.0% | 0.3 hours | 0.5 hours |

The results indicate that both concentrations of sodium sulfide are capable of significantly softening the nails, in vitro, in 3 hours or less.

EXAMPLE 4

Using Sodium Sulfide Formulation For Relieving Painful Ingrown Toenail.

To determine the efficacy of our new formulation for treating ingrown toenail, 46 subjects suffering from ingrown toenail are treated with sodium sulfide formulations having initial sulfide concentrations of 1.0 or 2.0%, in accordance with the procedure described in FIGS. 3, 4 and 5. The procedure is carried out once or twice per day and is continued for up to 7 days or until the toenail is sufficiently softened to permit easy trimming, resulting in pain relief. The days until attaining nail trimming or until attaining a 1-point pain reduction (based upon a 4-point pain scale) are presented in Table 3:
1=slight, 2=moderate, 3=moderately severe and 4=severe.

TABLE 3

Time until Trimming or Pain Reduction

| Initial Content of Sodium Sulfide Nonahydrate Hydrogels | Days Until Trimming | Days Until Trimming or 1-Point Pain Reduction |
| --- | --- | --- |
| 1% (twice/day application) | 4.2 | 3.1 |
| 2% (twice/day application) | 4.2 | 3.4 |
| 2% (once/day application) | 2.9 | 2.6 |

The results indicate that 1% and 2% sodium sulfide nonahydrate gels, retained on afflicted ingrown toenails by the delivery system described above, are capable of significantly softening nails, which allows easy trimming resulting in pain relief.

We claim:

1. A method for softening nails or for treating ingrown toenail, comprising contacting the nail with a stable sulfide-containing composition containing an inert atmosphere comprising:
   a) a sulfide, a polysulfide or mixtures thereof, of an alkali or an alkaline earth metal; and
   b) a carrier containing water, such that after maintaining the sulfide-containing composition at a temperature of about 37° to about 50° Celsius for about 2 weeks to one month, the sulfide content remaining in the sulfide-containing composition is about 90% to about 100% of the initial sulfide content; for a time effective to soften the nail, and optionally, trimming the nail or ingrown toenail.

2. A process for preparing a stable sulfide-containing composition containing an inert atmosphere comprising,
   a) initially treating water, by removing entrapped and dissolved gases therein that can decompose the sulfide; or alternatively, using treated water in which entrapped and dissolved gases have been removed that can decompose the sulfide;
   b) followed by dispersing an inert gas into said treated water to replace said entrapped and dissolved gases; and
   c) subsequently adding the sulfide and the carrier to the water prepared as in step b).

3. The process of claim 2 wherein in step (a), the water is initially treated by using agitation under vacuum to remove said entrapped and dissolved gases.

4. The process of claim 3 wherein the sulfide is a sulfide of an alkali earth metal.

5. The process of claim 2 wherein the sulfide is sodium sulfide.

6. The method of claim 1 wherein the sulfide is a sulfide of an alkali earth metal.

7. The method of claim 1 wherein the sulfide is sodium sulfide.

8. The method as claimed in claim 7 wherein the carrier containing water is a gel.

9. The method as claimed in claim 8 wherein the gel contains a non-ionic cellulosic material.

10. The method as claimed in claim 9 wherein the non-ionic cellulosic material is hydroxyethyl cellulose.

11. The method of claim 7 wherein the amount of sulfide in the composition is in the range from about 0.01 to about 10 percent (wt/wt of composition).

12. The method of claim 7 wherein the amount of sulfide in the composition is in the range from about 0.5 to about 5 percent (wt/wt of composition).

13. The method of claim 7 wherein the amount of sulfide in the composition is in the range from about 1 to about 3 percent (wt/wt of composition).

14. The method of claim 7 wherein the amount of sulfide in the composition is in the range from about 0.1 to about 2 percent (wt/wt of composition).

15. The method of claim 7 wherein the amount of sulfide in the composition is in the range from about 0.5 to about 1 percent (wt/wt of composition).

16. The method of claim 7 wherein the amount of sulfide in the composition is about 1 percent (wt/wt of composition).

* * * * *